United States Patent [19]

Grantham

[11] 4,241,020

[45] Dec. 23, 1980

[54] APPARATUS FOR BIOLOGICAL DECONTAMINATION AND SUBSEQUENT NEUTRALIZATION OF A SPACE

[75] Inventor: James I. Grantham, Raleigh, N.C.

[73] Assignee: Certek, Inc., Raleigh, N.C.

[21] Appl. No.: 916,199

[22] Filed: Jun. 16, 1978

[51] Int. Cl.³ .......................... A61L 2/20; A61L 2/26; G05D 7/00; G05D 16/00
[52] U.S. Cl. ................................... 422/109; 422/111; 422/112; 422/115; 422/116; 422/292; 422/305
[58] Field of Search .................... 422/30, 33, 36, 110, 422/111, 112, 119, 109, 115, 116, 292, 305, 306

[56] References Cited

U.S. PATENT DOCUMENTS

| | | | |
|---|---|---|---|
| 3,694,146 | 9/1972 | Roy et al. | 422/305 |
| 3,796,541 | 3/1974 | Gentil | 422/292 |
| 3,816,074 | 6/1974 | Decupper | 422/305 |
| 3,958,935 | 5/1976 | Kowol | 422/36 |
| 4,119,400 | 10/1978 | Kurz | 422/305 |

*Primary Examiner*—Bradley R. Garris
*Attorney, Agent, or Firm*—Larson, Taylor and Hinds

[57] ABSTRACT

An apparatus for the remote biological decontamination of a space with formaldehyde and subsequent generation of a formaldehyde neutralizing agent so as to permit immediate access to the space is disclosed. The apparatus is completely self-contained and includes a control mechanism for automatically sequencing the various steps in the biological decontamination of the space.

12 Claims, 6 Drawing Figures

U.S. Patent    Dec. 23, 1980    Sheet 1 of 3    4,241,020
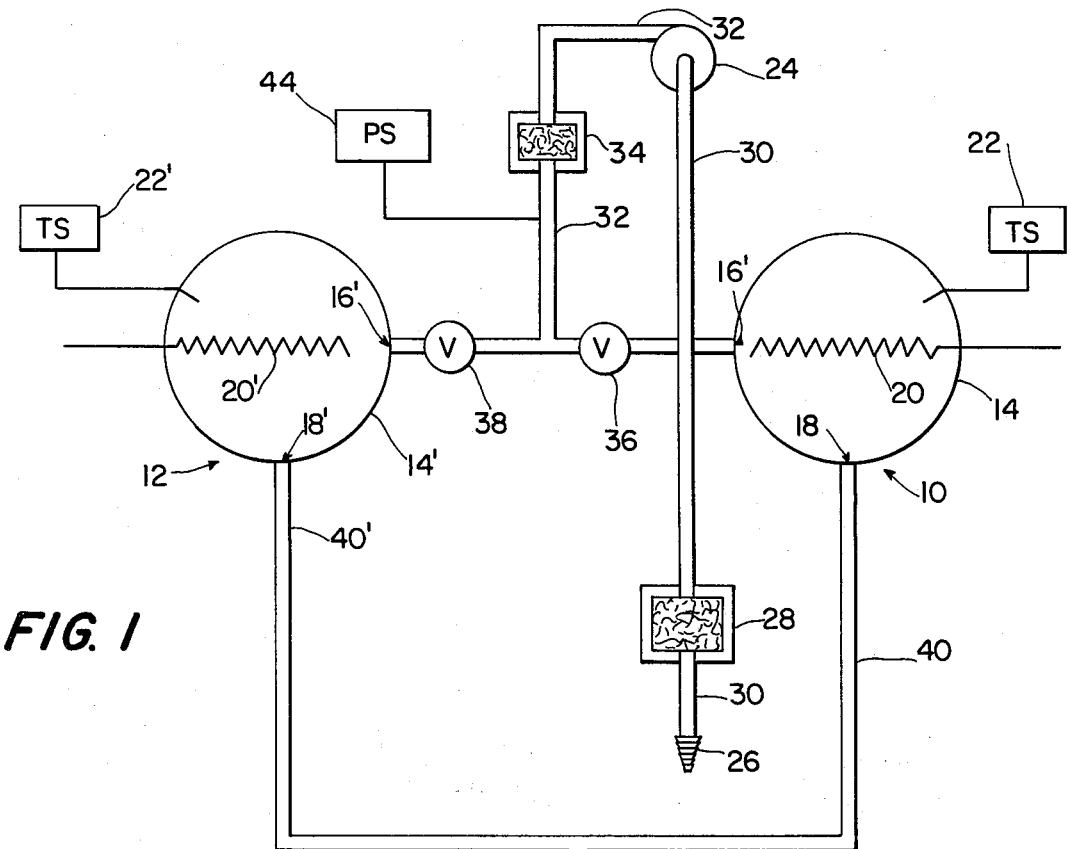
FIG. 1
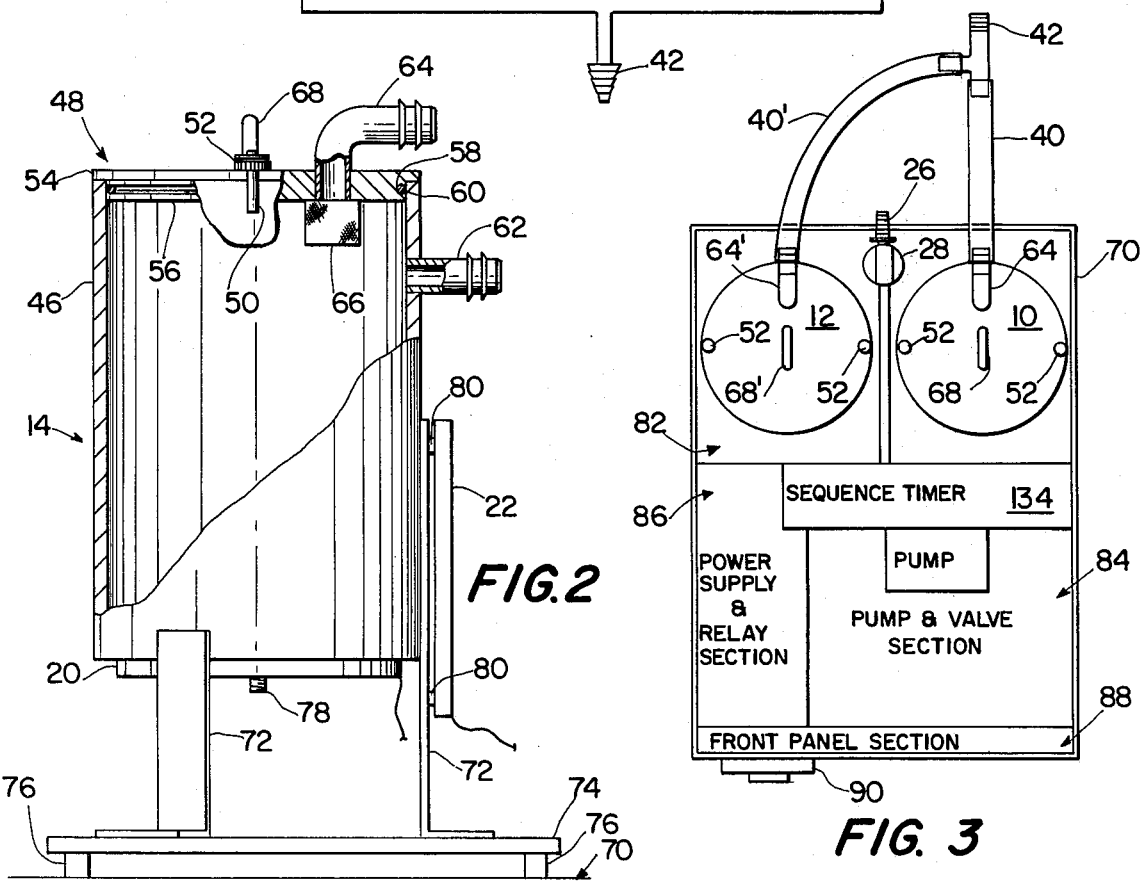
FIG. 2
FIG. 3

APPARATUS FOR BIOLOGICAL DECONTAMINATION AND SUBSEQUENT NEUTRALIZATION OF A SPACE

FIELD OF THE INVENTION

The present invention relates to an apparatus for the biological decontamination and subsequent neutralization of a space. In particular, the present invention relates to a formaldehyde generator for use in the automatic decontamination and subsequent neutralization of a space.

BACKGROUND OF THE INVENTION

The use of formaldehyde for biologically disinfecting and decontaminating spaces such as hospital rooms, manufacturing areas, biological safety cabinets, laminar flow work stations, pass-throughs, animal cages and animal hoods is well known in the art. Usually the formaldehyde is generated as a gas by heating a predetermined amount of para-formaldehyde and then permitting the gaseous formaldehyde to stay in the space for a predetermined amount of contact time. For most applications, it is recommended that 0.3 grams of flake para-formaldehyde per cubic foot of space be used and that a minimum contact time of one hour be allowed. The other parameters, such as the temperature and humidity which should be maintained in the space, and a procedure for using para-formaldehyde for biological decontamination are disclosed in various publications, such as the publication by U.S. Department of Health, Education, and Welfare (National Institutes of Health), entitled "Formaldehyde Decontamination of Laminar Flow Biological Safety Cabinets", which is incorporated herein by reference.

One general procedure known in the art comprises placing a predetermined amount of para-formaldehyde flakes in an electric skillet, plugging the skillet into a timer, and then placing the skillet in the space to be decontaminated. However, to my knowledge the NIH publication does not specify any neutralizing agent or procedure for neutralizing the formaldehyde so as to permit immediate access upon the termination of the decontamination procedure. In addition, an operator should continuously watch the skillet to ensure that no problems develop. Normally this observation must be conducted from outside of the space being decontaminated and remote from the formaldehyde generator. Should power be lost during the process, and the skillet cools, upon return of the power, vital time will be lost while the skillet is heated up to the proper temperature. Consequently, the exact stage at which the power was lost and whether all of the formaldehyde has been generated are unknown.

Since the only procedure mentioned in the NIH publication for removing the formaldehyde gas is simply to ventilate the decontaminated space to an outside environment, there developed in the field the use of two skillets, side-by-side, one for generating formaldehyde, and one for generating a neutralizing agent, such as powdered ammonium carbonate. The procedure is to first energize the skillet containing the formaldehyde and then after a certain generating time to unplug that skillet and then permit the formaldehyde to stay in the space during a predetermined contact time. At the end of this contact time, an operator would then energize the skillet containing the ammonium carbonate and keep it energized for a predetermined amount of time. Then, following a certain neutralizing contact time, the space should be completely neutralized and immediate access available. The disadvantages of such a procedure are obvious and include the necessity for an operator to be present at all stages and to initiate each of these stages. However, a non-obvious disadvantage of this procedure is that the ammonium carbonate is a highly unstable substance and is readily neutralized by the hot formaldehyde gas. As a result, as soon as the formaldehyde gas is generated, part of it will become immediately neutralized by the exposed ammonium carbonate. Consequently, the amount of formaldehyde gas actually decontaminating the space, and hence the extent of the decontamination, is unknown.

Apparatus for the in situ decontamination of a space and subsequent neutralization of the space are disclosed in the U.S. patents to Decupper, U.S. Pat. No. 3,816,074 and to Anderson, U.S. Pat. No. 3,898,038, both of which are incorporated herein by reference. However, the apparatus disclosed in these patents cannot be remotely operated or inspected and should a power failure occur, the stage at which the failure occurred will be unknown. In addition, the forms of apparatus depicted in these patents are designed for use only in relatively large spaces such as hospital rooms and cannot be used for decontaminating smaller spaces such as biological safety cabinets and animal cages. The patent to Roy et al, U.S. Pat. No. 3,694,146 does depict a formaldehyde gas generator for the remote generation of formaldehyde, but the device depicted therein does not provide any means for the subsequent neutralization of the formaldehyde nor the automatic control and sequence indication of the generator.

Consequently, there is a need for a completely portable formaldehyde biological decontamination and neutralization device that is automatically controlled, can be inspected remote from the space to be decontaminated, and is completely self-contained.

SUMMARY OF THE INVENTION

The present invention overcomes the foregoing and other disadvantages of the prior art, yet can be manufactured relatively inexpensively and is completely portable. The present invention permits the remote, automatic biological decontamination and subsequent neutralization of spaces while maintaining the integrity of the contained spaces. By automatically neutralizing the decontaminating formaldehyde gas, immediate access to the space being decontaminated is permitted. An indicator panel on an apparatus according to the present invention permits the exact stage of the decontamination/neutralization sequence to be readily determined. Because the apparatus according to the present invention is located remote from the space being decontaminated, visual verification of formaldehyde generation and of the neutralizing agent's generation is possible before entry into the space being decontaminated.

Other features and advantages of the present invention include a front panel for visually indicating the particular stage of operation of the device, an indication of loss of power and premature termination of the operating sequence, an indication of abnormal conditions, such as high pressure together with an automatic sequence termination, and a control system which automatically recycles the apparatus to a safe stage at any point in the operational sequence during which a problem develops.

In accordance with one embodiment of the invention, apparatus for automatically and remotely decontaminating a space with formaldehyde and subsequently neutralizing the formaldehyde comprises a formaldehyde generator and a neutralizing agent generator, each generator including a canister for containing a formaldehyde or a formaldehyde neutralizing gas generating substance, respectively, and having an opening therein, a gas tight cover for said opening, a gas inlet and outlet, and a heater means for heating said canister to generate formaldehyde gas or neutralizing gas, respectively. A pumping means is provided for discharging a gas under pressure, the suction of the pumping means being connectable in fluid communication with the space being decontaminated and the discharge being connectable in fluid communication selectively through the formaldehyde generator or the neutralizer generator to the space to be decontaminated. A fluid connecting means selectively connects the pumping means through only one of the formaldehyde generator and the neutralizer generator to the space to be decontaminated. The apparatus further comprises a control means for automatically controlling the sequencing of the apparatus through a first, formaldehyde generation stage during which the formaldehyde heater is actuated and the pumping means is energized and connected to the formaldehyde generator by the fluid connecting means; a second, formaldehyde contact stage during which the pumping means and both the heater means are de-energized; a third, neutralizer generation stage during which the neutralizer heater is actuated and the pumping means is energized and connected to the neutralizer generator by the fluid connecting means; and a fourth, neutralizer contact stage during which the pumping means and both the heater means are de-energized. The apparatus also includes a control panel for indicating the operating stage thereof.

Other features and advantages of the present invention will be discussed in or apparent from the description of the preferred embodiments of the invention found hereinbelow.

BRIEF DESCRIPTION OF THE DRAWINGS

FIG. 1 is a schematic block diagram of a biological decontamination and neutralization apparatus according to one embodiment of the present invention.

FIG. 2 is a side elevational view, partly in cross-section, of a gas generator.

FIG. 3 is a schematic layout, in plan view, of the housing of one embodiment of the present invention depicting the location of the various housing sections and of the components.

DETAILED DESCRIPTION OF THE PREFERRED EMBODIMENTS

Figure 4:
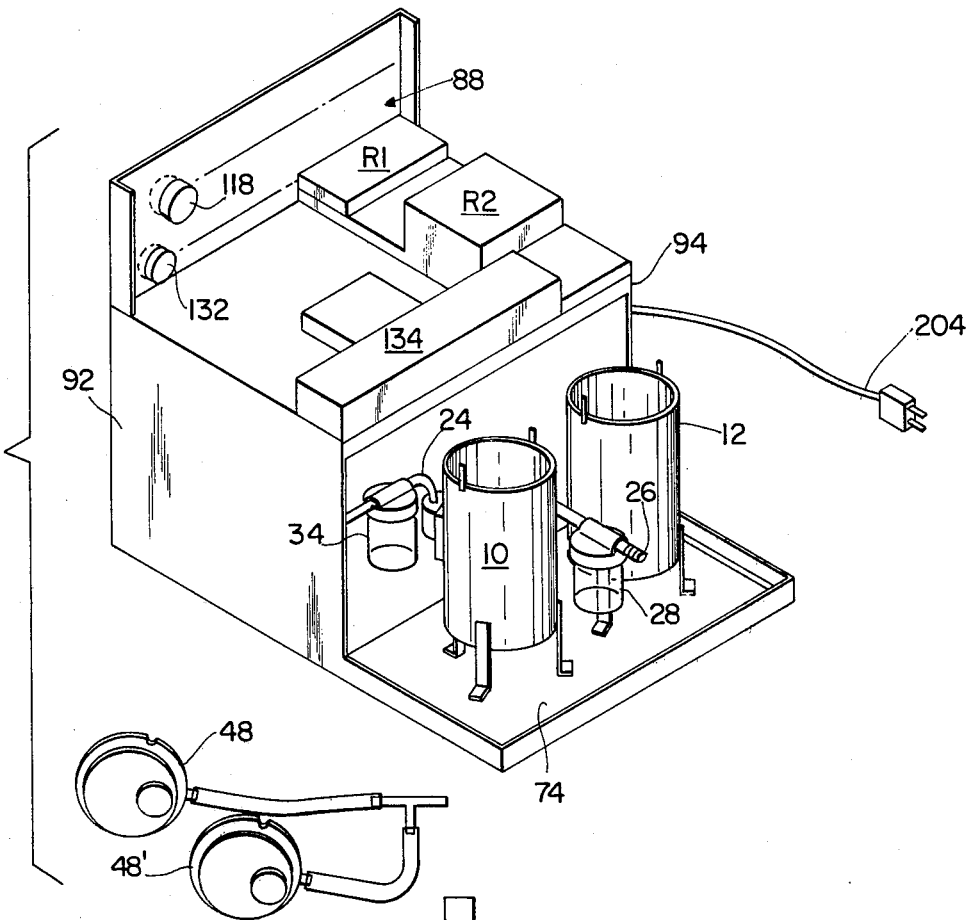
FIG. 4 is a perspective view, taken from the rear side with parts of the housing removed and parts of the generators disassembled, of the apparatus with some parts shown schematically.

With reference to the figures wherein like numerals depict like elements in the several views, an apparatus for automatically and remotely decontaminating a space with formaldehyde and subsequently neutralizing the formaldehyde according to the present invention is disclosed. With reference in particular to FIG. 1, a schematic diagram of the apparatus according to the present invention is depicted. The apparatus comprises a formaldehyde generator 10 and a neutralizing acid generator 12, which are substantially identical and the components of which are respectively designated by unprimed and primed numbers. Each generator includes a totally enclosable canister 14, 14' for containing, respectively, a formaldehyde gas generating substance or a formaldehyde neutralizing gas generating substance, a gas inlet 16, 16', a gas outlet 18, 18', and an electrical heater 20, 20' for heating canister 14, 14' to generate the respective gas. A temperature measuring means 22, 22' such as a thermocouple or thyristor measures the temperature of canister 14, 14' and controls the operation of heater 20, 20' within a predetermined range. For the formaldehyde canister 14, the temperature range is controlled around 450° F., and for the neutralizer canister 14', the temperature range is controlled around 350° F.

The apparatus also comprises an oilless, continuous duty pump 24, a pump suction nozzle 26, a conventional gas suction filter 28, and suction tubing 30 interconnecting pump 24, filter 28, and suction nozzle 26. The discharge of pump 24 is connected in fluid communication with discharge tubing 32 through a conventional gas discharge filter 34 to either the formaldehyde canister gas inlet 16 or the neutralizer canister gas inlet 16' through solenoid operated valves 36 and 38, respectively. The gas outlets 18 and 18' of formaldehyde canister 14 and neutralizer canister 14' are connected through tubing 40 and 40', respectively, to a discharge nozzle 42. In one embodiment of the present invention, a pressure detecting means 44 monitors the pump discharge pressure on the downstream side of discharge filter 34 so as to detect any abnormally high pressures between pump 24 and the space to be decontaminated. In another embodiment, a pressure differential or flow measuring means can be used to monitor the tubing for abnormal constrictions and flow.

With reference now to FIG. 2, a canister 14 which can be either the formaldehyde canister or the neutralizer canister is depicted. In one particularly preferred embodiment, canister 14 is comprised of a 5 inch high, 3½ inch diameter, stainless steel cylindrical container 46 having a capacity of 240 grams of para-formaldehyde. This size canister can be used to contain a sufficient amount of flake para-formaldehyde to decontaminate over 135 cubic feet of space. Container 46 has a typical wall thickness of 1/16 inch and has an open top so as to permit insertion of the flake para-formaldehyde or neutralizing agent and for inspection of the container to ensure that all of the added substance has been dissipated. A stainless steel top closure 48 is removably mounted on container 46 with means such as threaded mounting studs 50, carried by the container, and terminal nuts 52. The mounting studs 50 can project upwardly adjacent the periphery of top 48, or through indentations in the periphery of top 48. Top 48 is comprised of an upper portion 54 which may have a diameter equal to or slightly greater than the outside diameter of container 46, and an integral lower portion 56 having a diameter slightly less than the inner diameter of container 46. Lower portion 56 has a peripheral groove 58 containing a neoprene O-ring 60 so that a gas tight seal can be obtained when top 48 is securely mounted onto container 46. The gas inlet of container 46 is located near the top portion thereof and has inserted therein a ⅜ inch inner diameter ferruled tube or inlet tube 62 to which connecting tubing from the corresponding solenoid valve can be mounted with a gas tight force fit. The gas outlet from canister 14 is provided by an orifice in top 48 into which a ⅜ inch inner diameter ferruled elbow outlet tube 64 is mounted. A perforated screen 66 having exemplary dimensions of ¾ inch diameter and ¾ inch length is mounted to outlet tube 64 on the inside of top 48 so as to prevent any particulate from being discharged through outlet tube 64. A U-shaped handle 68 is mounted on the outside of top 48 to permit easy manipulation thereof.

Canister 14 is rigidly mounted inside of a housing 70 which contains the other components of the present apparatus. Mounted onto the bottom portion of container 46 are three equally spaced apart legs 72 which are rigidly mounted onto a mounting plate 74 that is, in turn, rigidly mounted to housing 70 with insulated mounts 76. Mounting plate 74 is preferably made from highly reflective aluminum so that the heat generated by canister 14 can be reflected back to it. By mounting container 46 in this manner, maximum heating thereof can be obtained while maintaining the surrounding environment at a relatively safe, cooler temperature. Legs 72 permit convective air flow (or in an alternative embodiment forced air flow resulting from a fan) around the bottom of canister 14. Electrical heater 20 is comprised of conventional, disc washer-type heaters which can be threaded onto a depending stud 78 mounted to the bottom of container 46. Similarly, temperature sensing means 22 can be mounted on threaded studs 80 which are, in turn, mounted onto one of the legs 72.

Referring now to FIGS. 3 and 4, housing 70 is shown in greater detail. As seen in FIG. 3, housing 70 is divided into three major internal compartments, a generator section 82 in which formaldehyde generator 10 and neutralizer generator 12 are located, a mechanical section 84 in which pump 24, solenoid valves 36 and 38, discharge filter 34, and much of the tubing is located, and an electrical section 86 in which the power supply, a control means for automatically controlling the sequencing of the apparatus and certain components thereof, and the wiring are located. Housing 70 also comprises a front panel section 88 which contains the indicating lights, the fuses, the operating switches, and a formaldehyde contact timer 90 that is adjustable by the operator. In one preferred embodiment, housing 70 is comprised of a steel cabinet 92 having a width of 12 inches, a height of 12 inches, and a depth of 20 inches and an aluminum chassis 94 for mounting the electrical components.

Figure 5:
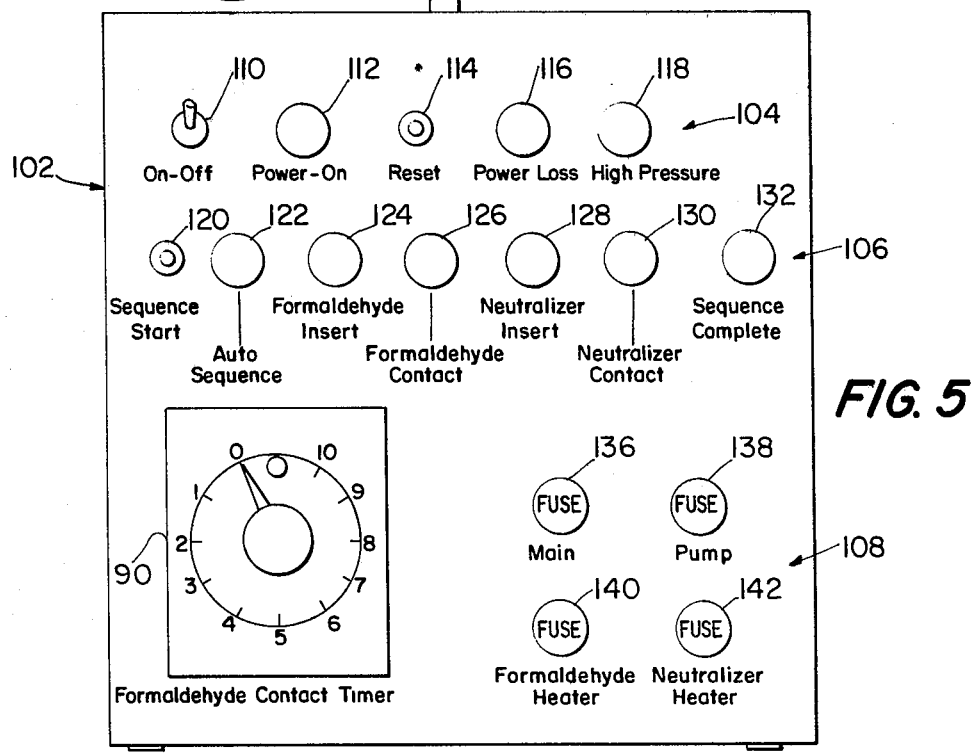
FIG. 5 is a front elevational view of the housing of one embodiment of the present invention showing the control panel and indicator lights thereon.

Before describing one embodiment of the control means and the operational sequence of the present apparatus, the front panel section 88 which mounts a control panel 102, as shown in FIG. 5, will be first described. Control panel 102 is comprised of a top row 104 and a second row 106 of indicator lights and switches located in the upper portion of control panel 102, a fuse section 108 located in the lower right hand corner of control panel 102, and contact timer 90 located in the lower left hand corner of control panel 102. Top row 104 contains, from left to right as shown in FIG. 5, a unit power on-off switch 110, a power-on indicating light 112, a reset switch 114, a power loss indicating light 116, and a high pressure light 118. The power-on switch 110 controls the main power of the apparatus and when power is being supplied to the control section, power-on light 112 is lit. Reset switch 114 is used to reset the control means before the start of the next operation of the apparatus. The operation of reset switch 114 will be described in greater detail hereinbelow. Power loss light 116, when lit, indicates that the control section has lost power, either at some stage during the automatic sequence of the control section or at the completion of the previous cycle. Finally, high pressure light 118 indicates that there is an abnormally high pressure in the discharge of pump 24 and that the control system has been de-energized and reset to the formaldehyde contact stage.

The second row 106 of lights and switches on control panel 102 contains, from left to right as shown in FIG. 5, a sequence start switch 120, an automatic sequence light 122, a formaldehyde insert light 124, a formaldehyde contact light 126, a neutralizer insert light 128, a neutralizer contact light 130, and a sequence complete light 132. Sequence start switch 120 and reset switch 114 are spring loaded, normally open, push button switches and are arranged in the indicated order since sequence start switch 120 is operated after reset switch 114. Sequence start switch 120 energizes a sequence timer 134, described in greater detail hereinbelow. Automatic sequence light 122, when lit, indicates that the control section is operating in the automatic mode. Formaldehyde insert light 124, when lit, indicates that the apparatus is currently in the stage when the formaldehyde gas is being generated and inserted into the space to be decontaminated. Formaldehyde contact light 126, when lit, indicates that the control section is in the stage when the formaldehyde gas has been sealed in the space to be decontaminated to ensure complete decontamination thereof. Neutralizer insert light 128, when lit, indicates that the control section is in the stage when the neutralizer gas is being generated and inserted into the space to be decontaminated. Neutralizer contact light 130, when lit, indicates that the control section is in the stage when the neutralizer gas has been sealed in the space to be decontaminated to ensure complete neutralization of the formaldehyde. Finally, the sequence complete light 132, when lit, indicates that the control section is in the stage following successful completion of the operation of the apparatus. The sequences of the aforementioned indicator lights are summarized in Table 1, hereinbelow.

Fuse section 108 permits front panel access to fuses protecting the major electrical equipment. A main system fuse 136 protects the entire control system and all the electrical equipment powered thereby. A pump fuse 138 protects pump 24 from overcurrent. Finally, a formaldehyde heater fuse 140 and a neutralizer heater fuse 142 protect these respective heaters from overcurrent.

Figure 6:
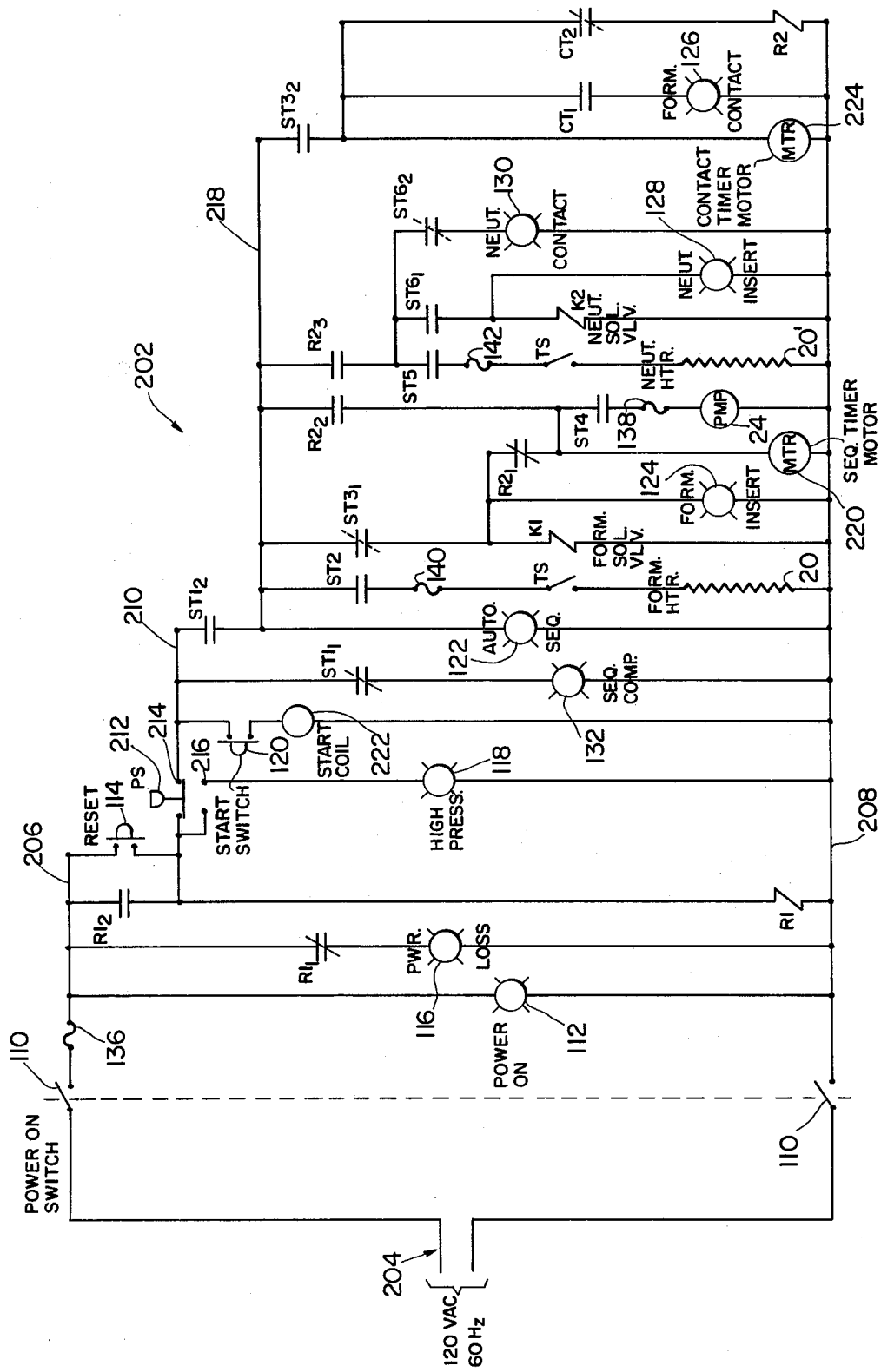
FIG. 6 is an electrical schematic diagram of one embodiment of the control means of the present invention.

Referring to FIG. 6, the electrical operation of the control means will now be discussed. Power is provided to a control means or control section 202 from a conventional electrical convenience outlet supplying 120 volts AC at 60 hertz through a power cord 204 (see also FIG. 4). Power-on switch 110 is a double pole, double throw switch which supplies line power to a hot rail 206 and a common rail 208. Main system fuse 136 is located just downstream of power-on switch 110 on hot rail 206 and, as mentioned above, protects control section 202 in the event of overcurrent. As soon as power-on switch 110 is switched to the "on" position, power-on indicating light 112 is energized to indicate that main system power is available to the remainder of control section 202. Reset switch 114 is similar to start switch 120 and is a push-button, spring-biased open switch, which when depressed, supplies system power from rail 206 around a normally open maintaining contact $R1_2$ to a main system relay R1. It is noted that the standard convention of designating a relay contact as being normally open or normally closed is the position of that contact when the relay is de-energized.

As soon as relay R1 is energized, maintaining contact $R1_2$ is closed and normally closed contact $R1_1$ is opened, thereby de-energizing power loss light 116. It can therefore be seen that whenever system power is lost, relay R1 will be de-energized, thereby opening maintaining contact $R1_2$ and closing contact $R1_1$. In this way, when power is resupplied, relay R1 will remain de-energized and the power loss light will remain lit until reset switch 114 is again depressed. It can also be seen that system power, once lost, is not resupplied to the remainder of control section 202 upon regaining power because the remainder of control section 202 is energized on the downstream side of maintaining contact $R1_2$ which is now open.

As mentioned above, power is supplied to the remainder of control section 202 from the downstream side of maintaining contact $R1_2$. This is accomplished through a reset rail 210. Reset rail 210 contains a pressure actuated switch 212 in series such that, upon actuation thereof, the remainder of the control section is de-energized. Pressure switch 212 is actuated when pressure detecting means 44 (FIG. 1) detects a high pressure in the discharge of pump 24. Pressure switch 212 is of a conventional type which is spring loaded into a first position 214 for normally supplying the downstream portion of reset rail 210. However, upon an over-pressure condition, pressure switch 212 is depressed to the second position 216 thereof thereby supplying power from reset rail 210 to high pressure light 118 and energizing this light. Since at the same time the remainder of the control section 202 is de-energized, as discussed hereinbelow, pump 24 will also be de-energized. When the excessive pressure bleeds off, pressure switch 212 is spring returned to its first position, thereby re-energizing pump 24. As should be readily apparent, this will result in pump 24 cycling with high pressure light 118 being alternately lit until the condition causing the high pressure is corrected. However, as explained hereinbelow, upon loss of power from reset rail 210, the sequence of the system after the formaldehyde insert stage will automatically be returned to the formaldehyde contact stage. Reset rail 210 also supplies power to normally open start switch 120 and to a pair of parallel sequence timer contacts controlled by a sequence timer 134, described in greater detail hereinbelow. These parallel contacts, $ST1_1$ and $ST1_2$ are of opposite positions so that when one is shut, the other is open. This is indicated by the dashed line through contact $ST1_1$. The position shown for the sequence timer contacts is when sequence timer 134 is in the reset position. As can be seen in FIG. 6, a system operating rail 218 is energized through "normally open" contact $ST1_2$.

At this point, sequence timer 134 will be described in greater detail. Sequence timer 134 is a conventional programming cam timer which can be of the type manufactured by Industrial Timer Corporation of Parsippany, N.J., and in particular, can be a Model RC8 Timer with A-30 gear rack manufactured by Industrial Timer Corporation. This timer is a single cycle, multi-cam timer of the type described in U.S. Pat. No. 2,776,009.

This timer has a heavy duty synchronous sequence timer motor 220 designed to provide a single timed electrical cycle upon the momentary actuation of a starting coil 222. A presently preferred model of a programming cam timer has six identical circular cams with a spring loaded cam follower which rides the circumference of the cam during the revolution thereof. As mentioned above, upon actuation of starting coil 222, a relay is actuated which withdraws a pawl from a notch in a circular control cam plate, thereby permitting revolution of the cams by sequence timer motor 220. These parts of timer 134 are not shown in the drawings. At the end of the single revolution, the pawl is again forced into the notch of the circular plate cam, thereby stopping the sequence timer motor. Each cam of the sequence timer motor can control a number of switches which can be normally shut or normally open. In this way, a single sequence timer can control a plurality of circuits.

Returning now to FIG. 6, the sequence timer contacts are designated with the letters "ST" together with the numbers from 1 to 6 to indicate the particular cam. If more than one switch is operated by a given cam, it is designated by a subscript, such as contacts $ST1_1$ and $ST1_2$. As mentioned above, operating rail 218 is energized through sequence timer contact $ST1_2$ which is shut immediately after the energization of starting coil 222. As now can be seen by FIG. 6, depression of start switch 120 energizes start coil 222 of sequence timer 134 from the reset rail 210. With the shutting of contact $ST1_2$, contact $ST1_1$ is opened, thereby de-energizing sequence complete light 132. Conversely, at the end of the operation of sequence timer 134, contact $ST1_1$ will be closed and thereby energize sequence complete light 132.

The operation of the remainder of control section 202, which is energized through operating rail 218, will now be explained. By properly programming sequence timer 134, upon the energizing of starting coil 222, contacts ST2, and ST4 are shut. In addition, "normally shut" contact $ST3_1$ remains shut and thereby energizes relay K1, energizes formaldehyde insert light 124, and energizes sequence timer motor 220 through normally closed contact $R2_1$, relay R2 being de-energized since contact $ST3_2$ is open. Relay K1 provides power to open formaldehyde solenoid valve 36, thereby permitting pump 24, which is energized through shut contacts $ST3_1$, $R2_1$, and ST4, to discharge air from pump suction nozzle 26 into formaldehyde generator 10 (see FIG. 1). In addition, formaldehyde heater 20 is energized through shut contact ST2. This condition continues until sequence timer 134 has been energized for a predetermined, preset amount of time (which is 45 minutes in a preferred embodiment). At the end of this time, switches ST2, $ST3_1$, and ST4 are opened and contact $ST3_2$ is shut. The shutting of this latter contact energizes a contact timer motor 224 and which shuts contact CT1, thereby energizing formaldehyde contact light 126. Contact timer motor 224 operates contact timer 90 described hereinabove and which has been pre-set by the operator. The opening of contact $ST3_1$ de-energizes the formaldehyde solenoid valve relay, K1, thereby resulting in the shutting of this valve, and the opening of contact ST2, resulting in the de-energizing of the formaldehyde heater 20. After the preset time on contact timer 90 has elapsed, the control section enters into the neutralizer insert stage. This occurs when contact timer 90 completes its cycle and shuts contact $CT_2$, thereby energizing relay R2 through shut switch $ST3_2$.

When relay R2 is energized, contact $R2_2$ is shut, which re-energizes sequence timer motor 220, the motor having been de-energized during the formaldehyde contact phase by the opening of switch $ST3_1$. Sequence timer motor 222 shuts contact ST4, ST5 and ST6, and opens contact $ST6_2$. Also when relay R2 is energized, switch $R2_3$ is shut which in turn supplies power to the neutralizer heater 20'; solenoid valve relay K2 and neutralizer insert light 128 through contacts ST5 and $ST6_1$, now shut. Shut contact ST4 re-energizes pump 24. Upon the completion of the preset time (which in a preferred embodiment is 45 minutes), the neutralizer insert stage comes to an end and the neutralizer contact stage automatically begins and runs for a preset time (which in one embodiment is for a one hour duration).

During the neutralizer contact stage, contacts ST4, ST5, and $ST6_1$ are opened and contact $ST6_2$ is shut. This results in pump 24 and neutralizer heater 20' being de-energized and the neutralization contact light 130 being energized.

It is noted, that the operation of both the formaldehyde heater 20 and the neutralizer 20' is through temperature actuated switches 226 and 226', respectively. As mentioned above, these switches are preset so as to keep the temperature of the formaldehyde canister 14 at 450° and the neutralizer canister 14' at 350°.

At the completion of the preset neutralizer contact time, the sequence timer will have completed its revolution and will be automatically stopped by the insertion of the aforementioned pawl. At this time, switch $ST1_1$ will close and switch $ST1_2$ will open, thereby respectively energizing the sequence completed light 132 and de-energizing system operating rail 218. The sequence of the switch positions is summarized in Table 2 hereinbelow.

In summary of the control section 202, it can be seen that it is comprised of a sequence timer motor having six switch cams and which is actuated by a start coil 222; a contact timer motor 224 which operates an operator preset neutralizer contact timer 90; and two system relays, R1 and R2.

Although the general system operation of the present invention has been described with respect to the operation of control section 202 hereinabove, some of these steps will be repeated as the procedure for decontaminating a space is described hereinbelow. The decontamination of a space is divided into three main stages, a preparation stage, a set-up stage, and an operation stage. Each of the steps in each stage will be described hereinbelow.

I. PREPARATION

1. Determine the size of the space to be decontaminated by measuring the height, width and depth in feet. Multiply the height times the width times the depth to determine the volume of the space in cubic feet.

2. Place a thermometer and hygrometer inside the enclosure and determine the temperature in degrees Fahrenheit and the relative humidity. Be sure that enough time is allowed for these gages to stabilize so that an accurate reading may be determined.

3. The temperature should remain between 60° and 90° F. for best results. Relative humidity must be held in excess of 60%. If the relative humidity is less than 60%, it must be increased by boiling water in the enclosure after the enclosure is sealed. Refer to any conventional Psychrometric Chart Method to determine the amount of water required. If spore strips are to be used, place them in the enclosure at this time.

4. Seal the enclosure. Some models of biological safety cabinets and animal cages provide plates to be used for this purpose. However, duct tape and polyethylene film (6 mil. minimum thickness) also provide a very adequate seal. Do not leave a light on inside the enclosure, as this will raise the temperature creating an undesirable elevation in pressure. Momentary lighting required to ascertain the temperature and relative humidity is permissible.

5. Refer to various National Institutes of Health Publications such as the one referred to hereinabove to determine the amount of flake para-formaldehyde and the length of the formaldehyde contact time that is required.

6. After determining the amount of para-formaldehyde required, the quantity of the neutralizer substance is determined. One such substance is ammonium carbonate and the amount needed to neutralize the determined amount of para-formaldehyde can be found by multiplying the number of grams of para-formaldehyde by the factor of 1.1.

II. SET-UP

1. Place rear of housing 70 as close to the formaldehyde insertion point as possible. Remove rear cover (not shown) from unit, exposing canisters 14.

2. Connect exhaust and supply hose from formaldehyde generator 10 to access openings to the space. It is recommended that the exhaust from the unit be as short as possible and the return tube be long so that the amount of formaldehyde polarization in the tubes is minimized. Make sure hoses are replaced periodically and are not plugged.

3. Remove the top from formaldehyde canister and place the amount of flake para-formaldehyde that was determined to be sufficient in Step #5 of the Preparation Section into the canister. Reinstall the top of the canister.

4. Remove the top from the neutralizer canister. Place the quantity of ammonium carbonate powder in this canister that was determined in Step #6 of the Preparation Section. Reinstall the top of the canister.

5. Set required "Contact Time" on the timer.

6. Plug the electrical cord of the formaldehyde generator into a convenience outlet which supplies 120 V, single phase, 60 cycle power supply.

III. OPERATION

1. Turn power-on switch 110 to the "ON" position. This should cause the Power-On and Power Loss lights 112 and 116 to energize. The Power Loss light 116 indicates that the generator has experienced the expected Power Loss after the previous cycle was completed and control section 202 de-energized.

2. Push reset switch 114. This programs control section 202 to begin the next cycle. Note that Sequence Complete light 132 is now activated, indicating that the previous cycle was successfully completed. If this light is not energized, sequence timer 134 did not reach its zero position from the previous cycle.

3. Push Start switch 120. This activates pump 24, formaldehyde heater 20, solenoid valve 36, and sequence timer 132. At this time, Form Insertion light 124 is energized, and formaldehyde generation and insertion begins.

4. After approximately 45 minutes elapsed time, pump 24, formaldehyde heater 20, and solenoid valve 36 will automatically be de-activated. Contact Timer 90 then controls the unit and formaldehyde contact light 126 is energized.

5. At the end of the Contact Time, neutralizer heater 20', pump 24, and solenoid valve 38 are activated and neutralization gas insertion will begin. The Neut. Insert light 128 will be activated. This cycle requires approximately 45 minutes.

6. At the end of the neutralization cycle and contact time, Sequence Complete light 132 is energized. Control section 202 remains in this configuration until the Power Switch is moved to the "OFF" position.

7. Prior to opening the decontaminated space, open formaldehyde canister 14 and neutralization canister 14 to ensure that both are empty and their respective contents were completely de-polymerized.

In the event power is lost at some point during the automatic sequence, reset switch 114 should be pressed and the lights which are energized should be noted. If automatic sequence light 122 and formaldehyde insert light 124 are lit, the power supply should be disconnected and sequence timer 134 should be manually positioned to the start position and the cycle restarted as described hereinabove. If automatic sequence light 122 and formaldehyde contact light 126 are energized, the system should be permitted to continue through the remainder of the stages. It is noted that a feature of the sequence timer 134 and of the control section's electrical design is that any time power is lost after the end of the formaldehyde insert stage, the system returns to the beginning of the formaldehyde contact stage.

As noted above, the actuation of the high pressure light 118 indicates that there is a constriction in the lines on the discharge of pump 24. Normally, pump 24 will cycle as the pressure is first built up and then bled off. All valves leading to the space to be decontaminated should be checked open and the lines checked to make sure they are not plugged or kinked. If the high pressure situation develops during the neutralizer insert stage, the system automatically returns to the formaldehyde contact stage as described hereinabove. The fact that there is an actual high pressure condition can be verified simply by turning off power switch 110, resetting contact timer 90 to its zero position, and turning power switch 110 on. If there is a constriction in the lines, and hence an actual high pressure condition, pump 24 will cycle.

Although the present invention has been described in detail with respect to a presently preferred embodiment, it is obvious to those of ordinary skill in the art that certain changes can be made without departing from the scope and spirit of the present invention. Thus, for example, a special purpose, digital computer system can easily replace the aforedescribed control system. In addition, the size of the various components can be changed so as to accommodate different size spaces to be decontaminated. Furthermore, the present invention can be easily incorporated into animal cages and hoods without departing from the spirit of the present invention.

Other modifications of and changes to the exemplary embodiments of the present invention will be obvious to those of ordinary skill in the art.

TABLE 1

Sequence of Indicator Lights Operation

| LIGHT | INDICATION WHEN LIT |
|---|---|
| Power On | Control section receiving power |
| Power Loss | Indicates that control section has lost power, either at some stage during the automatic sequence or at the completion of the previous cycle |
| Auto. Seq. | "Automatic Sequence": the generator is operating in the automatic mode |
| Form. Insert | "Formaldehyde Insertion": the stage when the formaldehyde gas is being generated and inserted into the space to be de-contaminated |
| Form. Contact | "Formaldehyde Contact": the stage when the formaldehyde gas has been sealed in the space to be de-contaminated to insure complete de-contamination |
| Neut. Insert | "Neutralizer Insertion": the stage when the neutralizer gas is being generated and inserted into the space to be de-contaminated |
| Neut. Contact | "Neutralizer Contact": the stage when the neutralizer gas has been sealed in the space to be de-contaminated to insure complete neutralization of the formaldehyde |
| Seq. Comp. | "Sequence Complete": the stage following successful completion of the generation's sequence |
| High Press. | "High Pressure": indicates that there is an abnormally high pressure in the discharge of the generator's pump and that the control system has been de-energized |

TABLE 2

Sequence of Switch Positions

|  | Form. Insert | Form. Contact | Neut. Insert | Neut. Contact | Timer Reset Power Off |
|---|---|---|---|---|---|
| R1$_1$ | OPEN | OPEN | OPEN | OPEN | SHUT |
| R1$_2$ | SHUT | SHUT | SHUT | SHUT | OPEN |
| R2$_1$ | SHUT | SHUT | OPEN | OPEN | SHUT |
| R2$_2$ | OPEN | OPEN | SHUT | SHUT | OPEN |
| R2$_3$ | OPEN | OPEN | SHUT | SHUT | OPEN |
| ST1$_1$ | OPEN | OPEN | OPEN | OPEN | SHUT |
| ST1$_2$ | SHUT | SHUT | SHUT | SHUT | OPEN |
| ST2 | SHUT | OPEN | OPEN | OPEN | OPEN |
| ST3$_1$ | SHUT | OPEN | OPEN | OPEN | SHUT |
| ST3$_2$ | OPEN | SHUT | SHUT | SHUT | OPEN |
| ST4 | SHUT | OPEN | SHUT | OPEN | OPEN |
| ST5 | OPEN | OPEN | SHUT | OPEN | OPEN |
| ST6$_1$ | OPEN | OPEN | SHUT | OPEN | OPEN |
| ST6$_2$ | SHUT | SHUT | OPEN | SHUT | SHUT |
| CT$_1$ | OPEN | SHUT | OPEN | OPEN | OPEN |
| CT$_2$ | SHUT | OPEN | SHUT | SHUT | SHUT |

I claim:

1. Apparatus for automatically and remotely decontaminating a space with formaldehyde and subsequently neutralizing the formaldehyde comprising, a housing containing:

a formaldehyde generator which includes a totally enclosable canister for containing a formaldehyde gas generating substance and having an access opening therein, a gas tight, removable cover for said access opening, gas inlet and outlet openings, and a heater means for heating said canister to generate formaldehyde gas;

a neutralizing agent generator which includes a totally enclosable canister for containing a formaldehyde neutralizing, gas generating substance and having an access opening therein, a gas tight, removable cover for said access opening, gas inlet and outlet openings, and a heater means for heating said canister to generate neutralizing gas; said formaldehyde generator and said neutralizer generator being mounted in said housing;

pumping means in said housing for discharging a gas under pressure, the suction of which is adapted to be connected in fluid communication with the space to be decontaminated, and the discharge of which is adapted to be selectively connected in fluid communication through said formaldehyde generator or said neutralizer generator to the space to be decontaminated;

fluid connecting means for selectively connecting said pumping means through only one of said formaldehyde generator and said neutralizer generator and connectable to the space to be decontaminated;

a control means in said housing for automatically controlling the supplying of power to the components of said apparatus and the sequencing of said apparatus through a first, formaldehyde generation stage during which said formaldehyde heater means is actuated and said pumping means is energized and connected to said formaldehyde generator by said fluid connecting means; a second, formaldehyde contact stage during which said pumping means and both said heater means are de-energized; a third, neutralizer generation stage during which said neutralizer heater means is actuated and said pumping means is energized and connected to said neutralizer generator by said fluid connecting means; and a fourth, neutralizer contact stage during which said pumping means and both said heater means are de-energized;

a control panel on said housing for externally indicating the particular stage in the operating sequence of said apparatus;

and said control means further including a system de-energizing means for preventing the resupplying of power to said control means after the power has been interrupted and a means for detecting a high-pressure condition in said fluid connecting means, and wherein after said control means has sequenced beyond said first stage of operation, said control means automatically returns to said second stage whenever power has been interrupted or whenever a high-pressure condition is detected.

2. Apparatus as claimed in claim 1 wherein said control means includes a first, preset sequence timer to control the length of said first, third and fourth stages and a second, operator-settable contact timer to control the length of said second stage.

3. Apparatus as claimed in claim 1 wherein said control panel includes indicator means for indicating after the resupplying of power to said control means that said control means has been de-energized and at what stage said control means is presently in.

4. Apparatus as claimed in claim 1 wherein said housing contains all of the other parts of said apparatus and is completely portable.

5. Apparatus as claimed in claim 1 wherein said fluid connecting means includes a system inlet nozzle connected in fluid communication to the suction of said pumping means, a system outlet nozzle connected in fluid communication to said gas outlet openings of said formaldehyde canister and said neutralizer canister, and flexible tubing removably connectable between said system outlet nozzle and the space to be decontaminated and between said system inlet nozzle and the space to be decontaminated, said tubing being storable in said housing when not in use.

6. Apparatus as claimed in claim 5 wherein said fluid connecting means includes a first remotely operated valve means for permitting or preventing fluid communication between said pumping means discharge through said formaldehyde generator to the space to be decontaminated and a second remotely operated valve means for permitting or preventing fluid communication between said pumping means discharge through said neutralizer generator to the space to be decontaminated, said first and second valve means being selectively operated by said control means; and wherein said fluid connecting means comprises a first conduit connecting said pumping means discharge and said formaldehyde canister gas inlet opening, and a second conduit connecting said pumping means discharge and said neutralizer canister gas inlet opening, and wherein said first and second valve means each comprise a solenoid operated valve, said first and second valve means are respectively located in said first and second conduits.

7. Apparatus as claimed in claim 1 wherein each of said formaldehyde and neutralizing canisters further is comprised of a plurality of legs for mounting said canister spaced from said housing.

8. Apparatus as claimed in claim 7 wherein in each of said formaldehyde and neutralizer canisters, said outlet opening is in said cover, said access opening is located at the top of said canister, and said inlet opening is located in the upper portion of said canister.

9. Apparatus as claimed in claim 8, wherein each of said formaldehyde and neutralizing canisters further includes a cylindrical container having said access opening in the top thereof and wherein said legs are mounted at the lower portion of said container so as to support said container in an upstanding position with said access opening at the top thereof.

10. Apparatus as claimed in claim 9, wherein said container has a completely open end to provide a rounded access opening, and further includes upstanding mounting members attached to the upper end thereof; and wherein said top is comprised of a disk shaped body having a diameter so as to fit within said container, a radial flange integral with the top portion of said body and having a diameter so as to extend beyond said access opening and engage the upper end of said container, means for cooperating with said mounting members so as to permit attachment of said top to said canister, and a peripheral seal mounted in the edge of said disk shaped body so as to sealingly engage the sides of said container when said top is mounted on said canister.

11. Apparatus as claimed in claim 9 and further including a heat reflective mounting plate and insulated mounts for supporting said mounting plate spaced from said housing, said canister legs in turn being mounted on said mounting plate.

12. Apparatus as claimed in claim 11 wherein said canister is metallic and said heater means is comprised of a heating element and a mounting means; and said canister further comprises means for cooperating with said heating element mounting means for mounting said heating element in contact therewith.

* * * * *